(12) United States Patent
Gasman

(10) Patent No.: US 6,276,937 B1
(45) Date of Patent: Aug. 21, 2001

(54) DENTURE ADHESIVE LINER

(75) Inventor: Robert C. Gasman, Montville, NJ (US)

(73) Assignee: Block Drug Company, Inc., Jersey City, NJ (US)

( * ) Notice: Subject to any disclaimer, the term of this patent is extended or adjusted under 35 U.S.C. 154(b) by 0 days.

(21) Appl. No.: 09/311,039

(22) Filed: Dec. 15, 1998

(51) Int. Cl.$^7$ ........................................... A61C 13/02
(52) U.S. Cl. ........................................ 433/168.1; 433/180
(58) Field of Search ..................... 433/168.1, 172, 433/180; 106/35

(56) References Cited

U.S. PATENT DOCUMENTS

| | | | |
|---|---|---|---|
| 3,838,513 | * 10/1974 | Katz et al. | 433/171 |
| 3,921,293 | 11/1975 | Keumurdji | 433/168.1 |
| 4,569,955 | * 2/1986 | Dhabhar | 523/120 |
| 4,677,139 | * 6/1987 | Feinmann et al. | 523/111 |
| 4,880,702 | * 11/1989 | Homan et al. | 428/354 |
| 5,256,064 | * 10/1993 | Riihimaki et al. | 433/141 |

FOREIGN PATENT DOCUMENTS

| | | |
|---|---|---|
| 364 865 | 11/1962 | (CH) . |
| 57-099511 | 6/1982 | (JP) . |
| WO 96 13244 | 5/1996 | (WO) . |

* cited by examiner

Primary Examiner—John J. Wilson
Assistant Examiner—Melba Bumgarner

(57) ABSTRACT

A denture adhesive liner contains a foamed, flexible, polymeric, self supporting layer that supports a denture adhesive and, optionally, a material for adhering the liner to a denture. The foamed self supporting layer helps provide better cushioning and a more effective gasket for the denture adhesive liner.

13 Claims, 1 Drawing Sheet

DENTURE ADHESIVE LINER

BACKGROUND OF THE INVENTION

1. Field of the Invention

The invention is directed to denture adhesive liners and to methods of making and using such liners.

2. Description of Related Art

Dentures and dental plates function as a substitute for all or part of missing teeth ordinarily found in the mouth. While dentures are usually carefully fitted for the user, the fit can change over time, causing discomfort and slippage. To alleviate the discomfort and to control the slippage, a denture adhesive may be applied to the denture.

Denture adhesives typically contain a material that forms a gasket between the denture and the gum line. Generally, the gasket-forming material is a water swellable gum or polymer. The gum or polymer hydrates and becomes tacky when introduced to the saliva in the oral cavity, thus holding the dentures in place.

The constant flow of saliva in the oral cavity, however, can cause premature washing away of the gum or polymer, so oils and petrolatum are also used in a denture adhesive to suspend the gum or polymer and so delay the washing away. The effective life of the gum or polymer during use is thereby increased.

Denture adhesives are usually applied as a cream or paste to the dentures before wearing. These highly viscous materials may be unpleasant to work with and may not provide an even hold at all points in the denture. Pressure gradients may cause the denture adhesive to migrate away from areas where the gum or other oral tissue is uncomfortably close to the denture material, thus reducing any cushioning effect of the adhesive at precisely the point where it is most needed. Migration of the denture adhesive material can also adversely affect the gasket that is formed by the adhesive between the denture and gums, thereby reducing the holding ability of the adhesive.

One alternative to traditional denture adhesives is a denture liner. A denture liner is a fixed, usually self supporting, layer coated with at least one layer of an adhesive material.

The self supporting layers used in past denture liners do not generally assist in the adhesive function. Rather, the self supporting layer holds the adhesive in place to limit or prevent migration of the adhesive, allowing an effective gasket to remain at the site selected by the user. Self supporting layers used in the art include plastic films, non woven fabrics, woven fabrics, and paper. Each of these materials can provide mechanical strength to support denture adhesive liner products and may prevent or reduce migration of the denture adhesive away from problem areas. But, these self supporting layer materials do little to enhance the strength of the gasket formed by the self supporting layer and the associated adhesive. In addition, these self supporting layers tend not to have the necessary flexibility and conformablilty required for fully comfortable denture adhesive products. The more inflexible the liner, of course, the greater the chance that the adhesives on the liner will fail to bond well to the irregular surfaces of the dentures and oral tissues. The gasket formed by the adhesive is correspondingly weaker, and may fail entirely.

A very early denture adhesive liner patent, U.S. Pat. No. 1,917,902 to Rowe, issued Jul. 11, 1933, describes a gum tragacanth adhesive on a cotton gauze self supporting layer. While cotton gauze is an acceptable material from a technical standpoint, the appearance of a product made in accordance with Rowe may have reduced its appeal in commercial use.

A commercial denture liner marketed under the name SEA BOND is described in U.S. Pat. No. 4,503,116 to Lapidus, issued Mar. 5, 1985. This liner uses a two-layer self supporting layer. The layers are bound together with a thermoplastic mixture of a polyethylene oxide and sodium alginate.

Another commercial product, marketed under the name TOUCH CORRECT, is discussed in U.S. Pat. No. 4,880,702 to Homan et al., issued Nov. 14, 1989. The patent discloses the use of adhesive outer layers containing an adhesive made from either a mix of polyethylene oxide and carboxymethyl cellulose or polyvinyl alcohol. The adhesive is held in place during use with a self supporting layer comprising microcrystalline wax, polyethylene oxide and carboxymethyl cellulose.

U.S. Pat. No. 5,158,825 to Altwirth, issued Oct. 27, 1992, is directed to a nonwoven fabric impregnated with a mixture of polyvinyl acetate and sodium alginate or carboxymethyl cellulose. This product is also on the market under the name FITTYDENT or SECURE.

U.S. Pat. No. 5,6568,586 to Rajaiah et al. (Rajaiah I) and European Patent Application No. 788,341 to Rajaiah et al. (Rajaiah II) are directed to compositions that may contain up to 70% of one or more therapeutic agents which are suitable for mucosal or topical administration. The patent describes a wide range of well known denture adhesive polymers, including salts of GANTREZ acid, Karaya gum, carboxymethyl cellulose, sodium alginate, and polyethylene oxide, but it specifically excludes polyvinyl acetate as a suitable adhesive component.

Rajaiah I calls for applying a weak pressure sensitive adhesive ("PSA"), polybutene, to one side of the liner product and then applying an aqueous solution of a partial GANTREZ salt adhesive to the other side to bond the liner to the dry denture adhesive material.

One recently published PCT application, WO 97US11,720 to Rajaiah et al., filed Jul. 3, 1997 and claiming priority from U.S. patent application Ser. No. 08/677,713, filed Jul. 8, 1996 (Rajaiah III), is directed to the use of a zinc Gantrez salt with a denture liner. The self supporting layer material may include polyester or polypropylene or nylon, nonwoven fabrics or fleece, paper, plastic, leather, microcrystalline wax, synthetic fibers, natural fibers and mixtures thereof.

Despite the progress that has been made in the use of denture liners, the search for more effective materials continues. There is still a strong need in the art for a liner that is both strong enough to withstand use in the oral environment and conformable enough to provide a well adhered gasket in use.

SUMMARY OF THE INVENTION

The principal object of the present invention therefore is to provide a denture liner that forms a good gasket between the denture and the oral mucosa and adheres well to both the denture and the oral mucosa.

It is an advantage of the invention that the liner is both strong and highly conformable. It can withstand use in the oral environment, and it is conformable enough to provide a firm gasket in use.

It is another advantage of the invention that the liner is self supporting, nontoxic and organoleptically acceptable.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and following the purpose of the invention, as embodied and broadly described herein, the invention provides a denture adhesive liner comprising a liner and at least one adhesive material. The liner is a foamed material and the adhesive is any of a number of acceptable adhesive materials.

To further achieve the foregoing objects and in accordance with the purpose of the invention, the invention further provides a method for making the denture adhesive liner by coating or otherwise incorporating at least one adhesive onto a foamed liner matrix.

BRIEF DESCRIPTION OF THE DRAWINGS

This specification concludes with claims particularly pointing out and distinctly claiming that which is regarded as the present invention. The objects and advantages of this invention may be more readily ascertained from the following description of a preferred embodiment when read in conjunction with the accompanying drawings.

DESCRIPTION OF THE PREFERRED EMBODIMENTS

Figure 1:
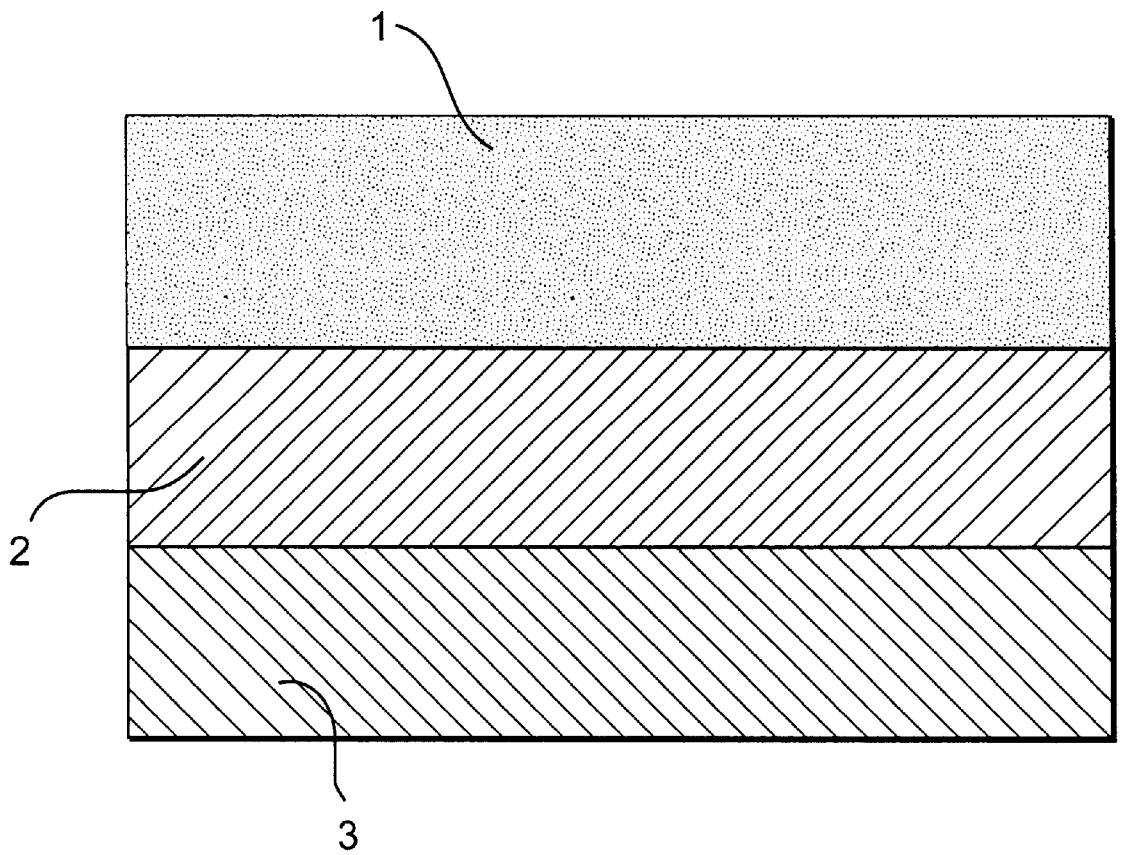
FIG. 1 is a schematic cross section of one embodiment of the denture liner of the invention.

Reference will now be made in detail to the presently preferred embodiments of the invention.

The denture liner of the invention comprises at least one self supporting layer. This self supporting layer comprises a foamed material, preferably a polymeric foam.

Foams, particularly polymeric foams, can be relatively rigid, inflexible materials, such as certain insulating or packing foams, or can be resilient, flexible materials such as foam rubber. The foam used in the liner of the invention may be any of the commonly used materials such as foam rubber, linear or network polymers, polyvinyl halides, polyurethanes, polyisocyanurates, polyphenols, polystyrene, cellulose acetate, polyethylene and other polyolefins. Since the invention is intended for oral use, nontoxic materials are preferable and either pleasant tasting or tasteless materials are most preferred. The foam should be resilient and soft during use and may contain open cells, closed cells, but preferably a combination of open and closed cells. The foamed material may be cut or molded into various desired shapes, either before or after combining the foamed material with the adhesive.

The foam may have any density, cell structure, cell size, cell geometry, and fraction of open cells desired to carry out the purposes of the invention. The foam should have enough thermal and environmental stability to remain intact in the mouth during ordinary use. The foam should be sufficiently cohesive so as not to crumble or separate during use and preferably acts to cushion any contact between the denture and the oral tissues.

The foamed self supporting layer generally does not have adhesive properties of its own, especially pressure sensitive adhesive properties, because such adhesion would tend to collapse the foam. Of course, since a permanent attachment to the mouth or denture is not contemplated with a denture liner, any adhesive properties should not cause permanent bonding to oral tissues or to the denture material.

The self supporting layer is characterized by its ability to maintain strength and provide integrity for the adhesive composition in the presence of water and/or saliva. The non-adhesive self supporting layer may include such materials as flexible foams made from polyester, polyethylene, polypropylene, rubber, polyurethane, flexible polyvinyl chloride, polystyrene, cellulose acetate, other cellulose esters and ethers, other low modulus thermoplastics, and mixtures thereof.

In addition to the self supporting layer, the invention comprises at least one adhesive material at least on one surface of the self supporting layer. The self supporting layer is a foamed material, and in a preferred embodiment of the invention it has a "skin" on its surface so that the adhesive material may be placed on the surface of one side of the self supporting layer without significant migration into the interior of the foamed material. Of course, the adhesive material may be coated on to both sides of the self supporting layer, preferably on top of a denture adhesive material as set forth herein.

The denture adhesive may comprise any known denture adhesive material compatible with the self supporting layer. Examples include, but are not limited to, polyvinyl alcohols, polyethylene oxides, karaya gum, methyl vinyl ether/maleic anhydride copolymers and hydrated derivatives thereof and partial salts thereof, either alone or in combination with an additive such as carboxymethyl cellulose or sodium alginate. The selection of an appropriate adhesive to combine with a particular self supporting layer is a matter of routine experimentation. As seen below in the examples, however, even closely related materials can have vastly different results in a denture liner. Some materials that have proven to be good denture adhesives without a self supporting layer have encountered difficulties in a denture liner delivery system.

The invention may also comprise additional components found in denture adhesives, such as natural gums, synthetic polymeric gums, adhesive materials commonly employed in denture stable compositions, additional synthetic polymers, mucoadhesive polymers, hydrophilic polymers, flavors, sweeteners, colorants, preservatives, thickeners, and polyethylene glycol and vehicles such as liquid petrolatum, petrolatum, mineral oil, propylene glycol, and glycerin. The liner of the invention may also contain other items not found in traditional denture adhesives such as plasticizers, bioadhesives, and even therapeutic actives designed for mucosal or topical administration.

One side of the liner may also comprise a pressure sensitive adhesive coating that adheres well to denture material, such as polybutenes, pressure sensitive silicone adhesives, polyacrylate ester pressure sensitive adhesives, tackified rubbers, natural polymers, and synthetic polymers.

A cross section of the liner of the invention is shown in FIG. 1. For ease of reference, the denture adhesive 1 is shown as laying on top of the foamed self supporting layer 2. A coating of material that adheres to denture material may be placed on one side 3 of the denture liner. Those skilled in the art will recognize that this coating is an optional, albeit preferred, feature of the invention. The coating 3 may be the same or different from the denture adhesive 1 and may be placed on the self supporting layer 2 in a separate manufacturing step from the denture adhesive 1. In an embodiment of the invention, a pressure sensitive adhesive is coated both on the bottom of the self supporting layer and either on top of the denture adhesive 1 or blended with the denture adhesive to form the top layer of the liner.

Preferably, the self supporting layer 2 is manufactured with a "skin" on at least one side that inhibits penetration of the foam by either the denture adhesive material or by the pressure sensitive adhesive. Excessive penetration into the foam could collapse the foam, reducing the effectiveness of the invention.

The denture liner may be made by preparing a denture adhesive formulation using techniques well known in the art and uniformly coating the adhesive material on the self supporting layer to form the denture liner. The liner may then be cut to the final desired shape. The optional coating material for adhering the liner to the denture material 3 may be coated on to the liner at any point in the process.

The denture adhesive (and the coating 3, if present) may be coated on the self supporting layer by any conventional coating techniques, such as by spraying (if the material is liquid or slurry or dissolved or suspended in a liquid such as water) or by sifting (if the denture adhesive is in powder form). If carrying out the coating process at elevated temperatures or pressures, penetration of the denture adhesive into, or through, the foamed self supporting layer is to be avoided.

In use, the liner may be placed on problem areas of the dentures before insertion into the mouth. Preferably, the liner either has a pressure sensitive adhesive layer 3 on the bottom that adheres to the denture material or has sufficient amounts of denture adhesive on the bottom to adhere to the denture. The presence of the denture adhesive on the bottom will help maintain the position of the liner on the denture if the liner is moistened before placement.

The self supporting layer, preferably a thermoplastic flexible foam, imparts enough mechanical strength to the liner to enable the liner to be easily removed intact from both the denture and the oral tissues when the denture wearer wishes to remove the liner.

The pressure sensitive adhesive side of the liner may be applied directly to a dry denture, leaving the denture adhesive side of the liner to adhere to the oral tissues. The highly compressible and conformable plastic foam self supporting material overcomes the deficiencies of prior art denture adhesive liners in that the adhesive faced plastic foam, owing to its easy compressibility, provides an excellent gasket. In addition the ready deformability of this adhesive faced plastic foam enables the adhesive facings to come into such intimate contact with the irregular surfaces of the dentures and the oral tissues that good bonding to both surfaces is achieved.

In addition to the denture adhesive, the self supporting layer and the pressure sensitive adhesive, the liner may comprise any additional ingredients appropriate for administration to the oral cavity, including teeth. Antibacterial agents, such as Triclosan, may be incorporated into any layer of the liner, as may ingredients such as anti-inflammatories, desensitizing agents, anesthetics, antifungals, *C. albicans* treatments, fluorides, and combinations thereof. Fluorides are especially helpful when the liner is used with a partial denture or dental prosthesis.

EXAMPLE 1

A thin layer of polyethylene oxide (Polyox®) film was laminated to one side of a 1 mm thick LDPE (low density polyethylene) plastic, double faced, pressure sensitive adhesive ("PSA") foam tape. The PSA face was adhered to one side of a small denture and the denture was inserted into the mouth of a volunteer. The polyethylene oxide film facing bonded well to the oral tissues, but the thickness of the liner was too great for comfort. The thickness also facilitated dislodgement. When the denture was removed, the adhesive liner was easily removed without leaving residue on the denture.

EXAMPLE 2

The polyethylene oxide film of Example 1 was laminated to one side of a 0.75 mm thick LDPE plastic double faced PS adhesive foam tape. The PSA face was adhered to one side of a small denture and the denture was inserted into the mouth of a volunteer. The denture remained comfortably in the mouth of the volunteer for the three hour duration of the test and was then removed.

EXAMPLE 3

A thin film of polyvinyl alcohol (PVA) was laminated to one side of a 0.75 mm thick PS double faced flexible LDPE foam tape. The PSA face of the resulting denture adhesive liner was applied to a denture, which was then inserted into the mouth of a volunteer. The PVA film side of the liner bonded to the oral tissues, specifically the upper palate. When the denture was removed, the denture adhesive liner was easily removed intact from the denture without leaving any residue. The polyvinyl alcohol film, however, did not bond as well to the palate as did the polyethylene oxide film used in the previous examples.

EXAMPLE 4

A 1.5 mil thick film of polyvinyl alcohol, Mono-5-ol n 9500, was laminated to one side of a 0.75 mm thick PS double faced flexible LDPE foam tape. The resulting liner was applied to a denture and inserted into the mouth of a volunteer as described above. Although the film held initially, the bond to the upper palate failed within about 5–10 minutes and could not be reestablished.

EXAMPLE 5

A powder adhesive comprising 49.6% by weight of the zinc, magnesium, and sodium partial salt of poly(methyl vinyl ether-co-maleic acid), 49.6% by weight of carboxymethyl cellulose, 0.4% by weight spray dried peppermint and 0.4% by weight spray dried spearmint was applied to one PSA side of a double faced LDPE foam tape. The powdered adhesive was pushed into the PSA layer until the PSA layer would accept no more. The excess powder was shaken off, and the resulting liner PSA side was applied to the denture. The coated strip held the denture in the mouth of a volunteer for the 3–4 hours of the test and was then removed.

EXAMPLE 6

A powder adhesive comprising 49.9% by weight of the sodium, calcium partial salt of poly(methyl vinyl ether-co-maleic acid), 49.9% by weight of carboxymethyl cellulose, 0.1% by weight spray dried peppermint and 0.1% by weight spray dried spearmint was applied to one side of a foam tape. The double salt coated liner, however, held for only about 5–10 minutes.

The purpose of the above description is to illustrate some embodiments of the present invention without implying a limitation. It will be apparent to those skilled in the art that various modifications and variations may be made in the apparatus or procedure of the invention without departing from the scope or spirit of the invention.

What is claimed is:

1. A denture adhesive liner for forming a gasket between a denture and the oral mucosa of a denture wearer, said liner comprising:

a. a self supporting layer of a foamed material having a first surface and a second surface; and b. a denture adhesive material coated on at least a portion of said first surface of said self supporting layer, wherein said self-supporting, foamed liner material maintains strength and provides integrity for said denture adhesive material in the presence of water and/or saliva, and said denture adhesive material adheres to the denture and/or the oral mucosa in use.

2. The denture adhesive liner of claim 1, further comprising a coating material on at least a portion of said second surface of said supporting layer.

3. The denture adhesive liner of claim 2, wherein said coating material comprises a pressure sensitive adhesive.

4. The denture adhesive liner of claim 1, wherein said foamed liner material comprises a flexible, partially closed cell, polymeric foam.

5. The denture adhesive liner of claim 1, wherein said denture adhesive material comprises a polymeric material selected from the group consisting of polyvinyl alcohols, polyethylene oxides, karaya gum, partial salts of methyl vinyl ether/maleic acid copolymers, and mixtures thereof.

6. The denture adhesive liner of claim 5, further comprising additional materials selected from the group consisting of carboxymethyl cellulose, sodium alginate, synthetic polymers, mucoadhesive polymers, hydrophilic polymers, thickeners, and mixtures thereof.

7. The denture adhesive liner of claim 1, wherein said denture adhesive material further comprises at least one agent selected from the group consisting of anti-inflammatories, antibacterial agents, desensitizing agents, anesthetics, antifungals, *C. albicans* treatments, fluorides, and combinations thereof.

8. The denture adhesive liner of claim 1, further comprising a coating material on at least a portion of said denture adhesive material.

9. The denture adhesive liner of claim 8, wherein said coating material comprises a pressure sensitive adhesive.

10. A method for making a denture liner for forming a gasket between a denture and the oral mucosa of a denture wearer, said method comprising the steps of:

a. providing a self supporting, foamed, flexible material having a first surface and a second surface; and b. adhering a denture adhesive material to at least a portion of the first surface of said self-supporting foamed flexible material, wherein said self-supporting, foamed liner material is able to maintain strength and provide integrity for said denture adhesive material in the presence of water and/or saliva, and said denture adhesive material is capable of adhering to the denture and/or the oral mucosa.

11. The method of claim 10 further comprising the step of coating at least one additional adhesive material onto the second surface of said foamed flexible material.

12. The method of claim 11, wherein said at least one additional adhesive material comprises a pressure sensitive material.

13. The method of claim 10, further comprising the step of coating at least one additional adhesive material on at least a portion of said denture adhesive material.

* * * * *